United States Patent
Cha et al.

(10) Patent No.: US 10,023,728 B2
(45) Date of Patent: Jul. 17, 2018

(54) LATEX COMPOSITION FOR DIP-FORMING INCLUDING CARBOXYLIC ACID MODIFIED-NITRILE BASED COPOLYMER LATEX AND DIP-FORMED ARTICLE PREPARED THEREFROM

(71) Applicant: LG Chem, Ltd., Seoul (KR)

(72) Inventors: Yu Jin Cha, Daejeon (KR); Jung Su Han, Daejeon (KR); Ji Hyun Kim, Daejeon (KR); Seung Uk Yeu, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/507,940

(22) PCT Filed: Oct. 20, 2015

(86) PCT No.: PCT/KR2015/011100
§ 371 (c)(1),
(2) Date: Mar. 1, 2017

(87) PCT Pub. No.: WO2016/064173
PCT Pub. Date: Apr. 28, 2016

(65) Prior Publication Data
US 2017/0283599 A1    Oct. 5, 2017

(30) Foreign Application Priority Data

Oct. 20, 2014  (KR) .................. 10-2014-0141775

(51) Int. Cl.
| | |
|---|---|
| *C08L 13/02* | (2006.01) |
| *C08F 222/10* | (2006.01) |
| *C08F 220/06* | (2006.01) |
| *C08L 9/04* | (2006.01) |
| *C08L 51/04* | (2006.01) |
| *C08L 15/00* | (2006.01) |
| *A61L 31/04* | (2006.01) |

(52) U.S. Cl.
CPC ............ *C08L 13/02* (2013.01); *A61L 31/049* (2013.01); *C08F 220/06* (2013.01); *C08F 222/1006* (2013.01); *C08L 9/04* (2013.01); *C08L 15/005* (2013.01); *C08L 51/04* (2013.01); *C08J 2313/02* (2013.01)

(58) Field of Classification Search
None
See application file for complete search history.

(56) References Cited

U.S. PATENT DOCUMENTS

| 6,031,042 | A | 2/2000 | Lipinski |
|---|---|---|---|
| 2006/0205881 | A1 | 9/2006 | Gozdiff et al. |
| 2007/0100063 | A1 | 5/2007 | Ozawa et al. |
| 2010/0152365 | A1 | 6/2010 | Han et al. |
| 2011/0229646 | A1* | 9/2011 | Kim ................. C08F 236/12 427/385.5 |
| 2014/0065336 | A1 | 3/2014 | Nakashima et al. |
| 2014/0302265 | A1 | 10/2014 | Yang et al. |

FOREIGN PATENT DOCUMENTS

| JP | 2006249430 A | 9/2006 |
|---|---|---|
| JP | 2010144163 A | 7/2010 |
| KR | 20100035191 A | 4/2010 |
| KR | 20120069222 A | 6/2012 |
| KR | 20120083031 A | 7/2012 |
| KR | 20130056505 A | 5/2013 |
| KR | 20140053859 A | 5/2014 |

OTHER PUBLICATIONS

Machine-generated English translation of KR 2012-0083031 A.*
English abstract of KR 2012-0083031 A.*
International Search Report from PCT/KR2015/011100, dated Jan. 28, 2016.
Search report from Office Action dated Jun. 12, 2018 for Chinese Application No. 2015800477954.

\* cited by examiner

*Primary Examiner* — Vu A Nguyen
(74) *Attorney, Agent, or Firm* — Lerner, David, Littenberg, Krumholz & Mentlik, LLP

(57) ABSTRACT

The present invention relates to a latex composition for dip-forming including two different types of carboxylic acid modified-nitrile based copolymer latex, and a dip-formed article prepared therefrom having excellent durability for sweat, and having high tensile strength and elongation percentage. Accordingly, the latex composition for dip-forming has excellent tensile strength, elongation percentage, stress and durability, and is useful in industries requiring these, for example, a rubber glove industry and the like.

15 Claims, No Drawings

LATEX COMPOSITION FOR DIP-FORMING INCLUDING CARBOXYLIC ACID MODIFIED-NITRILE BASED COPOLYMER LATEX AND DIP-FORMED ARTICLE PREPARED THEREFROM

CROSS-REFERENCE TO RELATED APPLICATIONS

The present application is a national phase entry under 35 U.S.C § 371 of International Application No. PCT/KR2015/011100 filed Oct. 20, 2015, which claims priority to Korean Patent Application No. 10-2014-0141775, filed on Oct. 20, 2014, the disclosures of which are incorporated herein by reference.

FIELD OF THE INVENTION

The present invention relates to a latex composition for dip-forming including two different types of carboxylic acid modified-nitrile based copolymer latex and a dip-formed article prepared therefrom having excellent durability for sweat and having high tensile strength and elongation percentage.

DESCRIPTION OF THE RELATED ART

Rubber gloves used in various fields such as housework, food industries, electronics industries and fields of medicine have been typically made by natural rubber forming. However, the use has been recently limited due to allergy problems caused by natural protein included in natural rubber, and a problem of unstable supply and demand. Consequently, rubber gloves made by dip forming a latex composition mixing sulfur and a vulcanization accelerator to synthetic rubber latex that does not induce allergy reactions, for example, carboxylic acid modified-nitrile based copolymer latex such as acrylic acid-acrylonitrile-butadiene copolymer latex have been widely used. Such rubber gloves made by mixing sulfur and a vulcanization accelerator have improved durability enough to be not damaged even when used for a long period of time since sulfur forms cross-linked bonds between polymer chains, and the strength of the rubber gloves may be enhanced.

However, when manufacturing rubber gloves using sulfur and a vulcanization accelerator, a long stir ripening process of 24 hours or longer needs to be included, and a problem of productivity decline is caused therefrom. In addition, rubber gloves mixing sulfur and a vulcanization accelerator as essential ingredients cause an unpleasant smell due to sulfur when continuing working with the gloves on for a long period of time, or decrease a value of commodities due to discoloration of the rubber gloves, and induce allergy reactions for some users resulting in skin disorders such as tingling.

Accordingly, researches have been progressed for manufacturing rubber gloves having favorable durability without causing problems such as displeasure from the use, discoloration, and allergy reactions by not using sulfur and a vulcanization accelerator. As one example, rubber gloves that use a latex composition for dip-forming including conjugated diene rubber latex and an organic peroxide, and that do not require a long stir ripening process and do not induce discoloration have been studied, however, there is a disadvantage in that process safety is very inferior since an organic peroxides is very harmful to the human body and may cause fires and explosions when heat or impacts are applied.

In addition, rubber gloves that do not induce allergy reactions caused by sulfur and a vulcanization accelerator without a long stir ripening process have been developed using a cross-linkable monomer to acrylic emulsion latex, however, the rubber gloves have a problem of being very sensitive to heat since the rubber gloves are made from acryl that is very vulnerable for heat.

In view of the above, while studying dip-formed articles (for example, rubber gloves) having excellent durability without requiring a long stir ripening process since sulfur and a vulcanization accelerator are not used, the inventors of the present invention have prepared a dip-formed article (for example, rubber gloves) from a latex composition for dip-forming including carboxylic acid modified-nitrile based copolymer latex (latex A) having a glass transition temperature of −30° C. to −5° C. and an average particle diameter of 100 nm to 200 nm and including a reactive compound, and carboxylic acid modified-nitrile based copolymer latex (latex B) having a glass transition temperature of −30° C. to −15° C. and an average particle diameter of 100 nm to 200 nm, identified that the dip-formed article exhibits excellent tensile strength, elongation percentage and durability, and completed the present invention.

PRIOR ART DOCUMENTS

Patent Documents (Patent Document 1) KR2014-0053859 A

DISCLOSURE OF THE INVENTION

Technical Problem

An object of the present invention is to provide a latex composition for dip-forming including two different types of carboxylic acid modified-nitrile based copolymer latex.

Another object of the present invention is to provide a dip-formed article prepared from the latex composition for dip-forming, and having excellent durability for sweat and having high tensile strength and elongation percentage.

Technical Solution

In view of the above, one embodiment of the present invention provides a latex composition for dip-forming including a) carboxylic acid modified-nitrile based copolymer latex having a glass transition temperature of −30° C. to −5° C. and an average particle diameter of 100 nm to 200 nm, and including a reactive compound; and b) carboxylic acid modified-nitrile based copolymer latex having a glass transition temperature of −30° C. to −15° C. and an average particle diameter of 100 nm to 200 nm. Another embodiment of the present invention provides a dip-formed article prepared from the latex composition for dip-forming.

Advantageous Effects

A latex composition for dip-forming according to the present invention includes two different types of carboxylic acid modified-nitrile based copolymer latex in a weight ratio of 3:7 to 8:2, and therefore, tensile strength, elongation percentage, stress and durability of the latex composition can be all superior.

Accordingly, a dip-formed article prepared from the latex composition for dip-forming can have excellent tensile strength, elongation percentage, stress and durability, and consequently, the carboxylic acid modified-nitrile based copolymer latex and the dip-formed article using the same can be useful in industries requiring these, for example, a rubber glove industry and the like.

MODE FOR CARRYING OUT THE INVENTION

Hereinafter, the present invention will be described in more detail in order to illuminate the present invention.

Terms or words used in the present specification and the claims are not to be interpreted limitedly to common or dictionary definitions, and shall be interpreted as meanings and concepts corresponding to technological ideas of the present invention based on a principle in which the inventors may suitably define the concepts of terms in order to describe the invention in the best possible way.

The present invention provides a latex composition for dip-forming including two different types of carboxylic acid modified-nitrile based copolymer latex, which does not require a long stir ripening process while not inducing allergy reactions since sulfur and a vulcanization accelerator are not included, and has excellent tensile strength, elongation percentage, stress (stress at 300% and 500% of elongation percentage) and durability.

The latex composition for dip-forming according to one embodiment of the present invention includes a) carboxylic acid modified-nitrile based copolymer latex having a glass transition temperature of −30° C. to −5° C. and an average particle diameter of 100 nm to 200 nm, and including a reactive compound (hereinafter, latex A); and b) carboxylic acid modified-nitrile based copolymer latex having a glass transition temperature of −30° C. to −15° C. and an average particle diameter of 100 nm to 200 nm (hereinafter, latex B).

The term "glass transition temperature (Tg)" used in the present invention means a point at which molecules in the latex start to move having activity due to a temperature, that is, a point at which the latex changes into a state having elasticity before changing from a solid state to a liquid state.

The latex A may have a glass transition temperature of −30° C. to −5° C. and an average particle diameter of 100 nm to 200 nm as described above, and preferably, the latex A may have a glass transition temperature of −30° C. to −10° C. When the glass transition temperature is lower than −30° C., tensile strength of a dip-formed article prepared from a latex composition for dip-forming including the latex A may significantly decrease, or wearability may decline due to stickiness, and when the glass transition temperature is higher than −5° C., a problem of having cracks in a dip-formed article prepared from a latex composition for dip-forming including the latex A may occur. In addition, when the latex A has an average particle diameter of 200 nm or greater, a process time may be long when preparing a dip-formed article prepared from a latex composition for dip-forming including the latex A, which leads to productivity decline, and tensile strength of the prepared dip-formed article may decrease.

The latex B may have a glass transition temperature of −30° C. to −15° C. and an average particle diameter of 100 nm to 200 nm as described above, and preferably, the latex B may have a glass transition temperature of −25° C. to −20° C. When the glass transition temperature is lower than −30° C., tensile strength of a dip-formed article prepared from a latex composition for dip-forming including the latex B may significantly decrease, or wearability may decline due to stickiness, and when the glass transition temperature is higher than −15° C., elongation percentage of a dip-formed article prepared from a latex composition for dip-forming including the latex B decreases leading to wearability decline.

In addition, when the latex B has an average particle diameter of 200 nm or greater, uniform mixing with the latex A may be difficult, and tensile strength of a dip-formed article prepared from a latex composition for dip-forming including the latex B may decrease.

Furthermore, the latex composition for dip-forming includes the latex A and the latex B in a weight ratio of 3:7 to 8:2.

When the weight ratio of the latex A is greater than 8 and the weight ratio of the latex B is less than 2, an effect of enhancing tensile strength of a dip-formed article prepared from a latex composition for dip-forming including the latex A and the latex B may be insignificant, and when the weight ratio of the latex A is less than 3, and the weight ratio of the latex B is greater than 7, elongation percentage and durability of a dip-formed article prepared from a latex composition for dip-forming including the latex A and the latex B may rapidly decrease.

Hereinafter, each of the carboxylic acid modified-nitrile based copolymer latex (latex A and latex B) according to the present invention will be described in more detail.

Carboxylic Acid Modified-Nitrile Based Copolymer Latex (Latex A)

The carboxylic acid modified-nitrile based copolymer latex according to one embodiment of the present invention (hereinafter, latex A) includes 0.1 parts by weight to 5 parts by weight of a reactive compound with respect to 100 parts by weight of a monomer mixture, and the monomer mixture includes 40% by weight to 89% by weight of a conjugated diene-based monomer; 10% by weight to 50% by weight of an ethylenically unsaturated nitrile-based monomer; and 0.1% by weight to 10% by weight of an ethylenically unsaturated acid monomer.

As described above, the conjugated diene-based monomer may be included in 40% by weight to 89% by weight, preferably in 45% by weight to 80% by weight, and more preferably in 50% by weight to 78% by weight. When the conjugated diene-based monomer is included in less than 40% by weight, a dip-formed article prepared from a latex composition for dip-forming including the conjugated diene-based monomer may become hard, and wearability may decline, and when included in greater than 89% by weight, a dip-formed article prepared from a latex composition for dip-forming including the conjugated diene-based monomer has inferior oil resistance and decreased tensile strength.

The conjugated diene-based monomer is not particularly limited, and examples thereof may include one or more types selected from the group consisting of 1,3-butadiene, 2,3-dimethyl-1,3-butadiene, 2-ethyl-1,3-butadiene, 1,3-pentadiene and isoprene. Preferably, the conjugated diene-based monomer may be 1,3-butadiene, isoprene or a combination thereof, and more preferably may be 1,3-butadiene.

The ethylenically unsaturated nitrile-based monomer may be included in 10% by weight to 50% by weight as described above, preferably in 15% by weight to 45% by weight, and more preferably in 20% by weight to 40% by weight. When the ethylenically unsaturated nitrile-based monomer is included in less than 10% by weight, a dip-formed article prepared from a latex composition for dip-forming including the ethylenically unsaturated nitrile-based monomer may have inferior oil resistance and decreased tensile strength may decrease, and when included in greater than 50% by weight, a dip-formed article prepared from a latex composition for dip-forming including the ethylenically unsaturated nitrile-based monomer may become hard, and wearability may decline.

The ethylenically unsaturated nitrile-based monomer is not particularly limited, and examples thereof may include one or more types selected from the group consisting of acrylonitrile, methacrylonitrile, fumaronitrile, α-chloronitrile and α-cyanoethyl acrylonitrile. Preferably, the ethylenically unsaturated nitrile-based monomer may be acrylonitrile, methacrylonitrile or a combination thereof, and more preferably acrylonitrile.

The ethylenically unsaturated acid monomer may be included in 0.1% by weight to 10% by weight as described above, preferably in 0.5% by weight to 9% by weight, and more preferably in 1% by weight to 8% by weight. When the ethylenically unsaturated acid monomer is included in less than 0.1% by weight, a dip-formed article prepared from a latex composition for dip-forming including the ethylenically unsaturated acid monomer may have decreased tensile strength, and when included in greater than 10% by weight, a dip-formed article prepared from a latex composition for dip-forming including the ethylenically unsaturated acid monomer may be hard, and wearability may decline.

The ethylenically unsaturated acid monomer may be an ethylenically unsaturated monomer having a carboxyl group, a sulfonic acid group or an acid anhydride group. Specifically, the ethylenically unsaturated acid monomer may be one or more types selected from the group consisting of an ethylenically unsaturated carboxylic acid monomer such as acrylic acid, methacrylic acid, itaconic acid, maleic acid and fumaric acid; a polycarboxylic acid anhydride such as maleic anhydride and citraconic anhydride; an ethylenically unsaturated sulfonic acid monomer such as styrenesulfonic acid; a partial ester monomer of an ethylenically unsaturated polycarboxylic acid such as monobutyl fumarate, monobutyl maleate and mono-2-hydroxypropyl maleate, and the like. Preferably, the ethylenically unsaturated acid monomer may be methacrylic acid. In addition, the ethylenically unsaturated acid monomer may be used in a form such as an alkali metal salt or an ammonium salt.

The reactive compound is included as one component of the latex A, and performs a role of enhancing tensile strength and durability of a dip-formed article prepared from a latex composition for dip-forming including the latex A without adding sulfur and a vulcanization accelerator, and as described above, may be included in 0.1 parts by weight to 5 parts by weight with respect to 100 parts by weight of the monomer mixture, and preferably in 0.5 parts by weight to 3 parts by weight. When the reactive compound is included in less than 0.1 parts by weight, tensile strength of a finally prepared dip-formed article may decrease, and when included in greater than 5 parts by weight, feel and wearability of a finally prepared dip-formed article may decline.

The reactive compound may be a compound having one or more types of reactive groups selected from the group consisting of a vinyl group, an epoxy group and a glycidyl group. Specifically, the reactive compound may be one or more types selected from the group consisting of a poly (tetramethylene ether)glycol diglycidyl ether compound, a 3-alkoxy-2-hydroxypropyl acrylate compound having 12 to 13 carbon atoms and a propylene glycol polybutyrene glycol monoacrylate compound.

In addition, the reactive compound may have a weight average molecular weight of 250 or larger, preferably 250 to 1000. When the reactive compound has a weight average molecular weight of smaller than 250, feel, wearability and tensile strength of a finally prepared dip-formed article may decline.

Furthermore, the latex A according to the present invention may further include 20% by weight or less of an ethylenically unsaturated monomer, and preferably, may further include 0.1% by weight to 20% by weight of an ethylenically unsaturated monomer.

The ethylenically unsaturated monomer is a monomer capable of being copolymerized with an ethylenically unsaturated nitrile monomer and an ethylenically unsaturated acid monomer included in the latex A, and is not particularly limited. Examples thereof may include one or more types selected from the group consisting of styrene, alkyl styrene, vinyl naphthalene; a fluoroalkylvinyl ether such as fluoroethyl vinyl ether; an ethylenically unsaturated amide monomer such as (meth)acrylamide, N-methylol (meth)acrylamide, N,N-dimethylol (meth)acrylamide, N-methoxymethyl (meth)acrylamide and N-propoxymethyl (meth)acrylamide; a non-conjugated diene monomer such as vinyl pyridine, vinyl norbornene, dicyclopentadiene and 1,4-hexadiene; an ethylenically unsaturated carboxylic acid ester monomer such as methyl (meth)acrylate, ethyl (meth) acrylate, butyl (meth)acrylate, 2-ethylhexyl (meth)acrylate, trifluoroethyl (meth)acrylate, tetrafluoropropyl (meth)acrylate, dibutyl maleate, dibutyl fumarate, diethyl maleate, methoxymethyl (meth)acrylate, ethoxyethyl (meth)acrylate, methoxyethoxyethyl (meth)acrylate, cyanomethyl (meth) acrylate, 2-cyanoethyl (meth)acrylate, 1-cyanopropyl (meth)acrylate, 2-ethyl-6-cyanohexyl (meth)acrylate, 3-cyanopropyl (meth)acrylate, hydroxyethyl (meth)acrylate, hydroxyethyl (meth)acrylate, hydroxypropyl (meth)acrylate, glycidyl (meth)acrylate and dimethylaminoethyl (meth) acrylate.

Meanwhile, the latex A may be prepared by additionally including additives such as a molecular weight modifier, an emulsifier, a polymerization initiator and an activator to a reactant including a monomer mixture including the conjugated diene-based monomer, the ethylenically unsaturated nitrile-based monomer and the ethylenically unsaturated acid monomer, and the reactive compound, and then emulsion polymerizing the result.

The emulsion polymerization is not particularly limited, and may be carried out using methods commonly known in the art, and a method of introducing a reactant including a monomer mixture including the conjugated diene-based monomer, the ethylenically unsaturated nitrile-based monomer and the ethylenically unsaturated acid monomer, and the reactive compound included in the latex A, and additives to a polymerization reactor at once, a method of continuously introducing the reactant, or a method of introducing some of the reactant at once and continuously introducing the remaining reactant, may be used.

A polymerization temperature during the emulsion polymerization is not particularly limited, and may be in a temperature range from 10° C. to 90° C., and preferably from 25° C. to 75° C. In addition, the moment to stop the polymerization may be a moment at which a polymerization conversion ratio is 90% or higher, preferably 93% or higher. In the emulsion polymerization, the latex A may be obtained by removing unreacted materials after stopping the polymerization, and adjusting a solid concentration and a pH.

The emulsifier used in the emulsion polymerization is not particularly limited, and those commonly known in the art may be used, and for example, anionic surfactants, nonionic surfactants, cationic surfactants, amphoteric surfactants and the like may be used. Specifically, one or more types of anionic surfactants selected from the group consisting of alkylbenzene sulfonate, aliphatic sulfonate, sulfonate ester of higher alcohol, α-olefin sulfonate and alkyl ether sulfonate ester may be preferable. The amount of the emulsifier used is not particularly limited, and may be properly adjusted by those skilled in the art, and for example, the emulsifier may be used in 0.3 parts by weight to 10 parts by weight with respect to 100 parts by weight of the whole monomer mixture. The emulsifier may be preferably used in 0.8 parts by weight to 9 parts by weight, and more preferably in 1.5 parts by weight to 6 parts by weight. When the amount of the emulsifier used is less than 0.3 parts by weight, stability during the emulsion polymerization may decline, and when the amount is greater than 10 parts by weight, foaming readily occurs during the emulsion polymerization, and a dip-formed article may not be readily prepared from a latex composition for dip-forming including latex A including the emulsifier.

The polymerization initiator is not particularly limited, and those commonly known in the art may be used, and for example, a radical initiator may be used. Examples of the radical initiator include one or more types selected from the group consisting of inorganic peroxides such as sodium persulfate, potassium persulfate, ammonium persulfate, potassium perphosphate and hydrogen peroxide; organic peroxides such as t-butyl peroxide, cumene hydroperoxide, p-menthane hydroperoxide, di-t-butyl peroxide, t-butylcumyl peroxide, acetyl peroxide, isobutyl peroxide, octanoyl peroxide, dibenzoyl peroxide, 3,5,5-trimethylhexanol peroxide and t-butylperoxy isobutyrate; azobisisobutyronitrile, azobis-2,4-dimethylvaleronitrile, azobiscyclohexane carbonitrile, and methyl azobisisobutyrate. Preferably, the polymerization initiator may be inorganic peroxides, and among these, persulfates may be particularly preferable. The amount of the polymerization initiator used is not particularly limited, and may be properly adjusted by those skilled in the art, and for example, the polymerization initiator may be used in 0.01 parts by weight to 2 parts by weight and preferably in 0.02 parts by weight to 1.5 parts by weight with respect to 100 parts by weight of the monomer mixture. When the polymerization initiator is used in less than 0.01 parts by weight, a polymerization rate decreases and preparing latex A may be difficult, and when the amount is greater than 2 parts by weight, a polymerization rate becomes too fast, and it may be difficult to control a degree of polymerization.

The activator is not particularly limited, and those commonly known in the art may be used, and for example, one or more types selected from the group consisting of sodium formaldehyde sulfoxylate, sodium ethylenediaminetetraacetate, ferrous sulfate, dextrose, sodium pyrophosphate and sodium sulfite may be used.

The molecular weight modifier is not particularly limited, and those commonly known in the art may be used, and examples thereof may include an α-methylstyrene dimer; mercaptans such as t-dodecyl mercaptan, n-dodecyl mercaptan and octyl mercaptan; halogenated hydrocarbons such as carbon tetrachloride, methylene chloride and methylene bromide; sulfur-containing compounds such as tetraethylthiuram disulfide, dipentamethylenethiuram disulfide and diisopropylxanthogene disulfide, and the like. The molecular weight modifier may be used either alone as one type or as a combination of two or more types. Preferably, mercaptans may be used, and t-dodecyl mercaptan may be particularly preferable. The amount of the molecular weight modifier used is not particularly limited, and may be properly adjusted by those skilled in the art, and for example, the molecular weight modifier may be used in 0.1 parts by weight to 2 parts by weight and preferably in 0.2 parts by weight to 1.5 parts by weight with respect to 100 parts by weight of the monomer mixture. More preferably, the amount may be from 0.3 parts by weight to 1 part by weight. When the molecular weight modifier is used in 0.1 parts by weight, physical properties of the latex A decline, and physical properties of a finally prepared dip-formed article may resultantly decline, and when used in greater than 2 parts by weight, polymerization stability may decline.

In addition, co-additives such as a chelating agent, a dispersant, a pH controlling agent, an oxygen absorber, a particle size modifier, an antioxidant and an oxygen scavenger may be additionally added as necessary during the polymerization.

Carboxylic Acid Modified-Nitrile Based Copolymer Latex (Latex B)

The carboxylic acid modified-nitrile based copolymer latex according to one embodiment of the present invention (latex B) includes 40% by weight to 89% by weight of a conjugated diene-based monomer; 10% by weight to 50% by weight of an ethylenically unsaturated nitrile-based monomer; and 0.1% by weight to 10% by weight of an ethylenically unsaturated acid monomer.

As described above, the conjugated diene-based monomer may be included in 40% by weight to 89% by weight, preferably in 45% by weight to 80% by weight, and more preferably in 50% by weight to 78% by weight. When the conjugated diene-based monomer is included in less than 40% by weight, a dip-formed article prepared from a latex composition for dip-forming including the conjugated diene-based monomer may become hard, and wearability may decline, and when included in greater than 89% by weight, a dip-formed article prepared from a latex composition for dip-forming including the conjugated diene-based monomer has inferior oil resistance and decreased tensile strength. The conjugated diene-based monomer may be the same as the conjugated diene-based monomer described above in the latex A, or may be included therein.

The ethylenically unsaturated nitrile-based monomer may be included in 10% by weight to 50% by weight as described above, preferably in 15% by weight to 45% by weight, and more preferably in 20% by weight to 40% by weight. When the ethylenically unsaturated nitrile-based monomer is included in less than 10% by weight, a dip-formed article prepared from a latex composition for dip-forming including the ethylenically unsaturated nitrile-based monomer may have inferior oil resistance and decreased tensile strength, and when included in greater than 50% by weight, a dip-formed article prepared from a latex composition for dip-forming including the ethylenically unsaturated nitrile-based monomer may become hard, and wearability may decline. The ethylenically unsaturated nitrile-based monomer may be the same as the ethylenically unsaturated nitrile-based monomer described above in the latex A, or may be included therein.

The ethylenically unsaturated acid monomer may be included in 0.1% by weight to 10% by weight as described above, preferably in 0.5% by weight to 9% by weight, and more preferably in 1% by weight to 8% by weight. When the ethylenically unsaturated acid monomer is included in less than 0.1% by weight, a dip-formed article prepared from a latex composition for dip-forming including the ethylenically unsaturated acid monomer may have decreased tensile strength, and when included in greater than 10% by weight, a dip-formed article prepared from a latex composition for dip-forming including the ethylenically unsaturated acid monomer may be hard, and wearability may decline. The ethylenically unsaturated acid monomer may be the same as the ethylenically unsaturated acid monomer described above in the latex A, or may be included therein.

In addition, like the latex A, the latex B may further include 20% by weight or less of an ethylenically unsaturated monomer, and preferably, may further include 0.1% by weight to 20% by weight of an ethylenically unsaturated monomer. The ethylenically unsaturated monomer may be same as the ethylenically unsaturated monomer described above in the latex A, or may be included therein.

Meanwhile, like the latex A, the latex B may be prepared through emulsion polymerization, and herein, the latex B may be prepared by additionally adding additives such as a molecular weight modifier, an emulsifier, a polymerization initiator and an activator to the conjugated diene-based monomer, the ethylenically unsaturated nitrile-based monomer and the ethylenically unsaturated acid monomer included in the latex B, and then emulsion polymerizing the result.

The emulsion polymerization is not particularly limited, and may be carried out using methods commonly known in the art, and a method of introducing a monomer mixture including the conjugated diene-based monomer, the ethylenically unsaturated nitrile-based monomer and the ethylenically unsaturated acid monomer included in the latex B, and additives to a polymerization reactor at once, a method of continuously introducing the monomer mixture, or a method of introducing some of the monomer mixture at once and continuously introducing the remaining monomer mixture, may be used.

A polymerization temperature during the emulsion polymerization is not particularly limited, and may be in a temperature range from 10° C. to 90° C., and preferably from 25° C. to 75° C. In addition, the moment to stop the polymerization may be a moment at which a polymerization conversion ratio is 90% or higher, preferably 93% or higher. In the emulsion polymerization, the latex B may be obtained by removing unreacted materials after stopping the polymerization, and adjusting a solid concentration and a pH.

The amount of the emulsifier used is not particularly limited, and may be properly adjusted by those skilled in the art, and for example, the emulsifier may be used in 0.3 parts by weight to 10 parts by weight with respect to 100 parts by weight of the monomer mixture. The emulsifier may be preferably used in 0.8 parts by weight to 9 parts by weight, and more preferably in 1.5 parts by weight to 6 parts by weight. When the amount of the emulsifier used is less than 0.3 parts by weight, stability during the emulsion polymerization may decline, and when the amount is greater than 10 parts by weight, foaming readily occurs during the emulsion polymerization, and a dip-formed article may not be readily prepared from a latex composition for dip-forming including latex B including the emulsifier. The emulsifier may be the same as the emulsifier described above in the latex A, or may be included therein.

The amount of the polymerization initiator used is not particularly limited, and may be properly adjusted by those skilled in the art, and for example, the polymerization initiator may be used in 0.01 parts by weight to 2 parts by weight and preferably 0.02 parts by weight to 1.5 parts by weight with respect to 100 parts by weight of the monomer mixture. When the polymerization initiator is used in less than 0.01 parts by weight, a polymerization rate decreases and preparing latex B may be difficult, and when the amount is greater than 2 parts by weight, a polymerization rate becomes too fast, and it may be difficult to control a degree of polymerization. The polymerization initiator may be the same as the polymerization initiator described above in the latex A, or may be included therein.

The amount of the molecular weight modifier used is not particularly limited, and may be properly adjusted by those skilled in the art, and for example, the molecular weight modifier may be used in 0.1 parts by weight to 2 parts by weight and preferably in 0.2 parts by weight to 1.5 parts by weight with respect to 100 parts by weight of the monomer mixture. More preferably, the amount may be from 0.3 parts by weight to 1 part by weight. When the molecular weight modifier is used in 0.1 parts by weight, physical properties of the latex B decline, and physical properties of a finally prepared dip-formed article may resultantly decline, and when used in greater than 2 parts by weight, polymerization stability may decline. The molecular weight modifier may be the same as the molecular weight modifier described above in the latex A, or may be included therein.

The activator may be the same as the activator described above in the latex A, or may be included therein.

In addition, co-additives such as a chelating agent, a dispersant, a pH controlling agent, an oxygen absorber, a particle size modifier, an antioxidant and an oxygen scavenger may be additionally added as necessary during the polymerization.

The latex composition for dip-forming according to the present invention including carboxylic acid modified-nitrile based copolymer latex (latex A) that includes the reactive compound and carboxylic acid modified-nitrile based copolymer latex (latex B) that does not include the reactive compound preferably includes the latex A and the latex B in 80% by weight to 99% by weight with respect to the total weight of the composition. In other words, the latex composition for dip-forming includes the latex A and the latex B, and total content of the latex A and the latex B included in the latex composition for dip-forming may be from 80% by weight to 99% by weight with respect to the total weight of the latex composition for dip-forming. The total content of the latex A and the latex B may be preferably from 85% by weight to 98% by weight, and more preferably from 88% by weight to 97% by weight.

The latex composition for dip-forming may further include one or more types of additives selected from the group consisting of an ionic cross-linking agent, a pigment, a viscosity agent and a pH controlling agent, in addition to the latex A and the latex B described above.

In addition, a solid concentration of the latex composition for dip-forming may be from 10% by weight to 40% by weight, preferably from 15% by weight to 35% by weight, and more preferably from 15% by weight to 30% by weight. A pH of the latex composition for dip-forming may be from 8 to 12, preferably from 9 to 11, and more preferably from 9.3 to 10.5.

Moreover, the present invention provides a dip-formed article prepared from the latex composition for dip-forming.

The dip-formed article according to one embodiment of the present invention has nitrogen content of 6.69% by weight to 8.94% by weight based on the total weight of the dip-formed article.

The dip-formed article according to one embodiment of the present invention is not particularly limited, and may be prepared using methods commonly known in the art, and for example, may be prepared using methods such as a direct dipping method, an anode coagulation dipping method and a Teague coagulation dipping method. Preferably, an anode coagulation dipping method may be used, and when the dip-formed article is prepared using an anode coagulation dipping method, there is an advantage in that a dip-formed article having a uniform thickness is capable of being obtained.

As a specific example, the dip-formed article may be prepared through the steps of immersing a hand-shaped dip mold in a coagulant solution to adhere a coagulant to a surface of the dip mold (step a); dipping the dip mold having the coagulant adhering on the surface in the latex composition for dip-forming to form a dip-forming layer (step b); and heat treating the dip-forming layer to cross-link a latex resin.

The step a is a step for adhering a coagulant on a surface of a hand-shaped dip mold and is not particularly limited, and may be carried out by immersing the dip mold in a coagulant solution for 1 minute or longer, taking out the dip mold, and drying the dip mold at 70° C. to 150° C.

The coagulant solution is a solution dissolving a coagulant in water, an alcohol or a mixture thereof, and typically, 5% by weight to 50% by weight of a coagulant may be included, and preferably, 10% by weight to 40% by weight of a coagulant may be included.

The coagulant is not particularly limited, and examples thereof may include metal halides such as barium chloride, calcium chloride, magnesium chloride, zinc chloride and aluminum chloride; nitrates such as barium nitrate, calcium nitrate and zinc nitrate; acetates such as barium acetate, calcium acetate and zinc acetate; and sulfates such as calcium sulfate, magnesium sulfate and aluminum sulfate. Preferable examples thereof may include calcium chloride, calcium nitrate or a combination thereof.

The step b is a step for forming a dip-forming layer from the latex composition for dip-forming according to the present invention on the dip mold to which the coagulant adheres, and the dip-forming layer may be formed by dipping the dip mold to which the coagulant adheres in the latex composition for dip-forming for 1 minute or longer, and taking out the dip mold.

The step c is a step for obtaining a dip-formed article by cross-linking a latex resin to the dip-forming layer, and may be carried out by heat treating the dip-forming layer.

The heat treatment is not particularly limited, and for example, may be accomplished by carrying out first heat treatment for 1 minute to 10 minutes at 70° C. to 150° C., and then carrying out second heat treatment for 5 minutes to 30 minutes at 100° C. to 180° C.

During the heat treatment, water first evaporates from the dip-forming layer, and by the latex resin of the dip-forming layer being cured through cross-linkage, a dip-formed article may be obtained.

The dip-formed article is not particularly limited, and may be used in various latex industries, and for example, may be used in one or more types of molded articles selected from the group consisting of examination gloves, condoms, catheters, industrial gloves, household gloves and health care products.

Hereinafter, the present invention will be described in more detail with reference to examples and test examples. However, the following examples and test examples are for illustrative purposes only, and the scope of the present invention is not limited thereto.

PREPARATION EXAMPLE 1

After a 10 L high-pressure reactor equipped with a thermometer, a cooler, a nitrogen gas inlet, and allowing continuous introduction of monomers, an emulsifier and a polymerization initiator was replaced with nitrogen, 2.5 parts by weight of sodium alkylbenzene sulfonate, 0.6 parts by weight of t-dodecyl mercaptan, 140 parts by weight of ion exchange water and 0.9 parts by weight of poly(tetramethylene ether)glycol diglycidyl ether were added to 100 parts by weight of a monomer mixture of 26.2% by weight of acrylonitrile, 68% by weight of 1,3-butadiene and 5.8% by weight of methacrylic acid, and the result was heated to 40° C. After raising the temperature, 0.25 parts by weight of potassium persulfate, a polymerization initiator, was added thereto to initiate polymerization, and when a conversion ratio reached 95%, the polymerization was stopped by introducing 0.1 parts by weight of sodium dimethyldithiocarbamate. Unreacted reactants were removed through a deodorizing process, and ammonia water, an antioxidant, an antifoaming agent and the like were added to prepare carboxylic acid modified-nitrile based copolymer latex (latex A-1) having a solid concentration of 45% and a pH of 7.0.

PREPARATION EXAMPLE 2

Carboxylic acid modified-nitrile based copolymer latex (latex A-2) was prepared in the same manner as in Preparation Example 1, except that acrylonitrile was used in 31.5% by weight, 1,3-butadiene in 62.5% by weight and methacrylic acid in 6% by weight.

PREPARATION EXAMPLE 3

Carboxylic acid modified-nitrile based copolymer latex (latex A-3) was prepared in the same manner as in Preparation Example 1, except that acrylonitrile was used in 33.5% by weight, 1,3-butadiene in 62.5% by weight and methacrylic acid in 4% by weight, and poly(tetramethylene ether)glycol diglycidyl ether was used in 3 parts by weight.

PREPARATION EXAMPLE 4

Carboxylic acid modified-nitrile based copolymer latex (latex A-4) was prepared in the same manner as in Preparation Example 1, except that acrylonitrile was used in 31.5% by weight, 1,3-butadiene in 66% by weight and methacrylic acid in 2.5% by weight, and poly(tetramethylene ether)glycol diglycidyl ether was used in 2 parts by weight.

PREPARATION EXAMPLE 5

Carboxylic acid modified-nitrile based copolymer latex (latex A-5) was prepared in the same manner as in Preparation Example 1, except that acrylonitrile was used in 35% by weight, 1,3-butadiene in 62.5% by weight and methacrylic acid in 2.5% by weight, and poly(tetramethylene ether)glycol diglycidyl ether was used in 2 parts by weight.

PREPARATION EXAMPLE 6

Carboxylic acid modified-nitrile based copolymer latex (latex A-6) was prepared in the same manner as in Preparation Example 1, except that acrylonitrile was used in 38% by weight, 1,3-butadiene in 57% by weight and methacrylic acid in 5% by weight, and poly(tetramethylene ether)glycol diglycidyl ether was used in 2 parts by weight.

PREPARATION EXAMPLE 7

After a 10 L high-pressure reactor equipped with a thermometer, a cooler, a nitrogen gas inlet, and allowing continuous introduction of monomers, an emulsifier and a polymerization initiator was replaced with nitrogen, 2.5 parts by weight of sodium alkylbenzene sulfonate, 0.6 parts by weight of t-dodecyl mercaptan and 140 parts by weight of ion exchange water were added to 100 parts by weight of a monomer mixture of 29% by weight of acrylonitrile, 64% by weight of 1,3-butadiene and 7% by weight of methacrylic acid, and the result was heated to 40° C. After raising the temperature, 0.25 parts by weight of potassium persulfate, a polymerization initiator, was added thereto to initiate polymerization, and when a conversion ratio reached 95%, the polymerization was stopped by introducing 0.1 parts by weight of sodium dimethyldithiocarbamate. Unreacted reactants were removed through a deodorizing process, and ammonia water, an antioxidant, an antifoaming agent and the like were added to prepare carboxylic acid modified-nitrile based copolymer latex (latex B) having a solid concentration of 45% and a pH of 8.0.

An average particle diameter, gel content (%) at 130° C., a glass transition temperature (Tg), surface tension (mN/m) and a molecular weight (kDa) of each carboxylic acid modified-nitrile based copolymer latex prepared in Preparation Example 1 to Preparation Example 4 were each measured. The results are shown in the following Table 1.

Herein, the glass transition temperature was measured according to common methods using a differential scanning calorimetry, and the average particle diameter was measured according to common methods using a laser scattering analyzer (Nicomp). In addition, as the gel content, each of the latex was dried for 48 hours or longer under a condition of 25° C. and a humidity of 60% to prepare a polymer film, and after cutting the polymer film into small pieces and measuring a weight ($W_0$), the pieces were placed in a container of #200 mesh, immersed in 200 ml of a methylethyl ketone (MEK) solution for 48 hours and then taken out, and dried in an oven at 130° C. to measure a weight ($W_1$). A ratio of the weight ($W_0$) of the polymer film placed in a container of #200 mesh and the weight ($W_1$) of the polymer film after drying in an oven measured as above was calculated and obtained as a percentage. The surface tension was obtained using a surface tension measuring device by horizontally hanging a small platinum ring, bringing the small platinum ring into contact with each of the sample liquids (latex), and measuring force required to remove the small platinum ring from the sample liquid when the small platinum ring was pulled. The molecular weight (kDa) was obtained by cutting each polymer film obtained by drying each of the latex at 130° C. into small pieces, immersing the polymer film piece in a tetrahydrofuran (THF) solution, filtering the polymer-dissolved liquid, comparing the liquid with a standard sample using gel permeation chromatography (GPC), and measuring a relative molecular weight.

TABLE 1

| Category | Average Particle Diameter (nm) | Gel Content (% at 130° C.) | Glass Transition Temperature (Tg, ° C.) | Surface Tension (mN/m) | Molecular Weight (kDa) |
| --- | --- | --- | --- | --- | --- |
| Preparation Example 1 | 117.4 | 68.7 | −16.4 | 41.55 | 9.0 |
| Preparation Example 2 | 106.6 | 72.06 | −17.31 | 40.09 | 7.3 |
| Preparation Example 3 | 128.5 | 66.15 | −18.29 | 40.78 | 6.5 |
| Preparation Example 4 | 121.3 | 58.63 | −25.45 | 39.65 | 9.7 |
| Preparation Example 5 | 118.2 | 66.89 | −19.1 | 41.82 | 8.3 |
| Preparation Example 6 | 122.0 | 87.18 | −9.5 | 37.12 | 6.0 |
| Preparation Example 7 | 123.8 | 40.1 | −25.8 | 33.1 | 19.8 |

TABLE 1-continued

EXAMPLE 1

1) Latex Composition for Dip-Forming

The carboxylic acid modified-nitrile based copolymer latex (latex A-1) that includes a reactive compound prepared in Preparation Example 1, and the carboxylic acid modified-nitrile based copolymer latex (latex B) that does not include a reactive compound prepared in Preparation Example 7 were mixed in a weight ratio of 5:5, and prepared, and 2.0 parts by weight of a 1.25% potassium hydroxide solution, a proper amount of distilled water, 1 parts by weight of titanium oxide and 1.5 parts by weight of zinc oxide were added and mixed thereto to prepare a latex composition for dip-forming having a solid concentration of 15% and a pH of 9.8. Herein, the parts by weights were based on 100 parts by weight of the latex composition for dip-forming.

2) Preparation of Dip-Formed Article 12 parts by weight of calcium nitrate, 87.9 parts by weight of distilled water and 0.1 parts by weight of a wetting agent (Teric 320, Huntsman Corporation, Australia) were mixed to prepare a coagulant solution. Herein, the parts by weights were based on 100 parts by weight of the coagulant solution. A hand-shaped ceramic mold was immersed in the coagulant solution for 10 seconds, taken out, and dried for 4 minutes at 80° C. to apply the coagulant on the hand-shaped ceramic mold.

After that, the coagulant-applied mold was immersed in the latex composition for dip-forming for 10 seconds, taken out, then dried for 2 minutes at 80° C., and then immersed in water for 1 minute. The mold was dried again for 3 minutes at 80° C., and then cross-linked for 20 minutes at 120° C. The cross-linked dip-forming layer was peeled off from the hand-shaped mold to obtain a dip-formed article in a glove form.

EXAMPLE 2

A latex composition for dip-forming and a dip-formed article were prepared in the same manner as in Example 1, except that carboxylic acid modified-nitrile based copolymer latex (latex A-2) prepared in Preparation Example 2 was used instead of the carboxylic acid modified-nitrile based copolymer latex (latex A-1) used in Preparation Example 1.

EXAMPLE 3

A latex composition for dip-forming and a dip-formed article were prepared in the same manner as in Example 1, except that the carboxylic acid modified-nitrile based copolymer latex (latex A-1) prepared in Preparation Example 1 was not used, and carboxylic acid modified-nitrile based copolymer latex (latex A-3) prepared in Preparation Example 3 and carboxylic acid modified-nitrile based copolymer latex (latex B) prepared in Preparation Example 7 were mixed in a weight ratio of 6:4, and used.

EXAMPLE 4

A latex composition for dip-forming and a dip-formed article were prepared in the same manner as in Example 1, except that the carboxylic acid modified-nitrile based copolymer latex (latex A-1) prepared in Preparation Example 1 was not used, and carboxylic acid modified-nitrile based copolymer latex (latex A-4) prepared in Preparation Example 4 and carboxylic acid modified-nitrile based copolymer latex (latex B) prepared in Preparation Example 7 were mixed in a weight ratio of 6:4, and used.

EXAMPLE 5

A latex composition for dip-forming and a dip-formed article were prepared in the same manner as in Example 1, except that the carboxylic acid modified-nitrile based copolymer latex (latex A-1) prepared in Preparation Example 1 was not used, and carboxylic acid modified-nitrile based copolymer latex (latex A-5) prepared in Preparation Example 5 and carboxylic acid modified-nitrile based copolymer latex (latex B) prepared in Preparation Example 7 were mixed in a weight ratio of 6:4, and used.

EXAMPLE 6

A latex composition for dip-forming and a dip-formed article were prepared in the same manner as in Example 1, except that carboxylic acid modified-nitrile based copolymer latex (latex A-5) prepared in Preparation Example 5 was used instead of the carboxylic acid modified-nitrile based copolymer latex (latex A-1) used in Preparation Example 1.

EXAMPLE 7

A latex composition for dip-forming and a dip-formed article were prepared in the same manner as in Example 1, except that the carboxylic acid modified-nitrile based copolymer latex (latex A-1) prepared in Preparation Example 1 was not used, and carboxylic acid modified-nitrile based copolymer latex (latex A-5) prepared in Preparation Example 5 and carboxylic acid modified-nitrile based copolymer latex (latex B) prepared in Preparation Example 7 were mixed in a weight ratio of 4:6, and used.

EXAMPLE 8

A latex composition for dip-forming and a dip-formed article were prepared in the same manner as in Example 1, except that the carboxylic acid modified-nitrile based copolymer latex (latex A-1) prepared in Preparation Example 1 was not used, and carboxylic acid modified-nitrile based copolymer latex (latex A-5) prepared in Preparation Example 5 and carboxylic acid modified-nitrile based copolymer latex (latex B) prepared in Preparation Example 7 were mixed in a weight ratio of 3:7, and used.

EXAMPLE 9

A latex composition for dip-forming and a dip-formed article were prepared in the same manner as in Example 1, except that the carboxylic acid modified-nitrile based copolymer latex (latex A-1) prepared in Preparation Example 1 was not used, and carboxylic acid modified-nitrile based copolymer latex (latex A-6) prepared in Preparation Example 6 and carboxylic acid modified-nitrile based copolymer latex (latex B) prepared in Preparation Example 7 were mixed in a weight ratio of 8:2, and used.

COMPARATIVE EXAMPLE 1

A latex composition for dip-forming and a dip-formed article were prepared in the same manner as in Example 1, except that the carboxylic acid modified-nitrile based copolymer latex (latex A-1) prepared in Preparation Example 1 was not used, and only carboxylic acid modified-nitrile based copolymer latex (latex B) prepared in Preparation Example 7 was used.

COMPARATIVE EXAMPLE 2

A latex composition for dip-forming and a dip-formed article were prepared in the same manner as in Example 9, except that the carboxylic acid modified-nitrile based copolymer latex (latex B) prepared in Preparation Example 7 was not used, and only the carboxylic acid modified-nitrile based copolymer latex (latex A-6) prepared in Preparation Example 6 was used.

COMPARATIVE EXAMPLE 3

A latex composition for dip-forming and a dip-formed article were prepared in the same manner as in Example 8, except that the carboxylic acid modified-nitrile based copolymer latex (latex A-5) prepared in Preparation Example 5 and the carboxylic acid modified-nitrile based copolymer latex (latex B) prepared in Preparation Example 7 were mixed in a weight ratio of 2:8, and used.

COMPARATIVE EXAMPLE 4

A latex composition for dip-forming and a dip-formed article were prepared in the same manner as in Example 9, except that the carboxylic acid modified-nitrile based copolymer latex (latex A-6) prepared in Preparation Example 6 and the carboxylic acid modified-nitrile based copolymer latex (latex B) prepared in Preparation Example 7 were mixed in a weight ratio of 9:1, and used.

TEST EXAMPLE

In order to compare and analyze physical properties of each of the dip-formed articles prepared in Examples 1 to 9 and Comparative Examples 1 to 4, Max load (N), tensile strength (MPa), elongation percentage (%), stress at 300% of elongation percentage (MPa), stress at 500% of elongation percentage (MPa) and durability of each of the dip-formed articles were measured. The results are shown in the following Table 2.

1) Max Load (N), Tensile Strength, Elongation Percentage, Stress at 300% and Stress at 500%

Each of the dip-formed articles was prepared into a dumbbell-type specimen in accordance with the ASTM D-412, and after pulling the specimen at a crosshead speed of 500 mm/min using a universal testing machine (UTM) (model name: 4466, Instron) in accordance with the ASTM D638, the point at which the each specimen was cut was measured. Max load (N) represents external force applied to the specimen at the time when the specimen was cut, and tensile strength was calculated by the following Mathematical Formula 1. In addition, elongation percentage (%) was calculated by the following Mathematical Formula 2, and as stress (MPa) at 300%, tensile strength of the specimen when elongated by three times from the initial length was measured, and as stress (MPa) at 500%, tensile strength of the specimen when elongated by five times from the initial length was measured.

TENSILE STRENGTH (kgf/mm$^2$) = $\dfrac{\text{LOAD VALUE (kgf)}}{\text{THICKNESS (mm)} \times \text{WIDTH (mm)}}$ [Mathematical Formula 1]

ELONGATION PERCENTAGE (%) = $\dfrac{\text{LENGTH AFTER ELONGATION}}{\text{INITIAL LENGTH}} \times 100$ [Mathematical Formula 2]

2) Durability

After each of the dip-formed articles was cut into an S-shaped specimen and prepared, each of the specimens was immersed in an artificially-made sweat solution, stretching the specimen to a percentage of 200% with respect to the initial length, and then shrinking were repeated at a rate of once every two seconds, and the number of times to the point of the specimen being cut was measured.

TABLE 2

| Category | Max load (N) | Tensile Strength (MPa) | Elongation percentage (%) | Stress (MPa, at 300%) | Stress (MPa, at 500%) | Durability (Times) |
|---|---|---|---|---|---|---|
| Example 1 | 14.1 | 30.0 | 516.4 | 6.6 | 26.03 | 325 |
| Example 2 | 13.2 | 28.4 | 498.5 | 6.8 | 28.21 | 447 |
| Example 3 | 13.1 | 30.8 | 465.9 | 7.2 | — | 520 |
| Example 4 | 6.9 | 15.5 | 539.0 | 4.5 | 11.37 | 894 |
| Example 5 | 7.2 | 16.1 | 533.9 | 4.8 | 12.90 | 916 |
| Example 6 | 8.9 | 19.1 | 522.6 | 5.6 | 16.52 | 277 |
| Example 7 | 9.1 | 20.5 | 527.0 | 7.0 | 23.87 | 208 |
| Example 8 | 12.6 | 28.7 | 524.9 | 6.9 | 27.1 | 214 |
| Example 9 | 10.9 | 24.4 | 409.9 | 9.8 | — | 1444 |
| Comparative Example 1 | 4.3 | 102 | 424.9 | 5.2 | — | 143 |
| Comparative Example 2 | 9.2 | 20.9 | 405.5 | 9.3 | — | 171 |
| Comparative Example 3 | 9.7 | 22.3 | 404.0 | 9.5 | — | 111 |
| Comparative Example 4 | 8.2 | 17.1 | 548.4 | 4.8 | 12.19 | 199 |

As shown in Table 2, the dip-formed articles of Example 1 to Example 9 prepared from a latex composition for dip-forming including the two different types of carboxylic acid modified-nitrile based copolymer latex according to the present invention exhibited excellent Max load, tensile strength, elongation percentage, stress (at 300% and 500%) and durability compared to the dip-formed articles of Comparative Example 1 to Comparative Example 4.

Specifically, the dip-formed articles of Example 1 to Example 9 prepared from a latex composition for dip-forming including the two different types of carboxylic acid modified-nitrile based copolymer latex according to the present invention exhibited significantly excellent properties in the Max load, the tensile strength, the elongation percentage, the stress (at 300% and 500%) and the durability compared to the dip-formed articles of Comparative Example 1 and Comparative Example 2 prepared from a latex composition for dip-forming including one type of the carboxylic acid modified-nitrile based copolymer latex. Particularly, in the stress (at 500%) test, the dip-formed articles of Comparative Example 1 and Comparative Example 2 were cut before reaching 500% and measured values were not obtained, whereas the dip-formed articles of Examples 1 to 9 according to the present invention exhibited an excellent stress property (at 500%).

In addition, when comparing Example 8 and Example 9 and Comparative Example 3 and Comparative Example 4 prepared under a condition different only in a ratio of the two types of carboxylic acid modified-nitrile based copolymer latex, Example 8 and Example 9 according to the present invention exhibited excellent properties in all of the Max load, the tensile strength, the elongation percentage, the stress and the durability, however, Comparative Example 3 and Comparative Example 4 were not balanced in the above-mentioned properties.

Accordingly, by including two different types of carboxylic acid modified-nitrile based copolymer latex, the latex composition for dip-forming according to the present invention is capable of forming a dip-formed article having excellent tensile strength, elongation percentage, stress and durability.

What is claimed is:

1. A latex composition for dip-forming comprising:
    a) carboxylic acid modified-nitrile based copolymer latex having a glass transition temperature of −30° C. to −5° C. and an average particle diameter of 100 nm to 200 nm, and including a reactive compound; and
    b) carboxylic acid modified-nitrile based copolymer latex having a glass transition temperature of −30° C. to −15° C. and an average particle diameter of 100 nm to 200 nm, wherein the reactive compound is not included,
    wherein the composition includes the a) carboxylic acid modified-nitrile based copolymer latex and the b) carboxylic acid modified-nitrile based copolymer latex in a weight ratio of 3:7 to 8:2, and wherein the reactive compound is a compound having one or more types of reactive groups selected from the group consisting of a vinyl group, an epoxy group and a glycidyl group.

2. The latex composition for dip-forming of claim 1, wherein the a) carboxylic acid modified-nitrile based copolymer latex includes 0.1 parts by weight to 5 parts by weight of the reactive compound with respect to 100 parts by weight of a monomer mixture, and the monomer mixture includes 40% by weight to 89% by weight of a conjugated diene-based monomer; 10% by weight to 50% by weight of an ethylenically unsaturated nitrile-based monomer; and 0.1% by weight to 10% by weight of an ethylenically unsaturated acid monomer, and
    wherein the b) carboxylic acid modified-nitrile based copolymer latex includes 40% by weight to 89% by weight of a conjugated diene-based monomer; 10% by weight to 50% by weight of an ethylenically unsaturated nitrile-based monomer; and 0.1% by weight to 10% by weight of an ethylenically unsaturated acid monomer.

3. The latex composition for dip-forming of claim 2, wherein the reactive compound is one or more types selected from the group consisting of a poly(tetramethylene ether) glycol diglycidyl ether compound, a 3-alkoxy-2-hydroxypropyl acrylate compound having 12 to 13 carbon atoms and a propylene glycol polybutyrene glycol monoacrylate compound.

4. The latex composition for dip-forming of claim 2, wherein the reactive compound has a weight average molecular weight of 250 to 1000.

5. The latex composition for dip-forming of claim 2, wherein the conjugated diene-based monomer is one or more types selected from the group consisting of 1,3- butadiene, 2,3-dimethyl-1,3-butadiene, 2-ethyl-1,3-butadiene, 1,3-pentadiene and isoprene.

6. The latex composition for dip-forming of claim 2, wherein the ethylenically unsaturated nitrile-based monomer is one or more types selected from the group consisting of acrylonitrile, methacrylonitrile, fumaronitrile, α-chloronitrile and α-cyanoethyl acrylonitrile.

7. The latex composition for dip-forming of claim 2, wherein the ethylenically unsaturated acid monomer is an ethylenically unsaturated monomer having a carboxyl group, a sulfonic acid group or an acid anhydride group.

8. The latex composition for dip-forming of claim 2, wherein the ethylenically unsaturated acid monomer is one or more types selected from the group consisting of acrylic acid, methacrylic acid, itaconic acid, maleic acid, fumaric acid, maleic anhydride, citraconic anhydride, styrenesulfonic acid, monobutyl fumarate, monobutyl maleate and mono-2-hydroxypropyl maleate.

9. The latex composition for dip-forming of claim 2, wherein the a) carboxylic acid modified-nitrile based copolymer latex and the b) carboxylic acid modified-nitrile based copolymer latex each further includes 0.1% by weight to 20% by weight of an ethylenically unsaturated monomer.

10. The latex composition for dip-forming of claim 9, wherein the ethylenically unsaturated monomer is one or more types selected from the group consisting of styrene, alkyl styrene, vinyl naphthalene, fluoroethyl vinyl ether, (meth)acrylamide, N-methylol (meth)acrylamide, N,N-dimethylol (meth)acrylamide, N-methoxymethyl (meth)acrylamide, N-propoxymethyl (meth)acrylamide, vinyl pyridine, vinyl norbornene, dicyclopentadiene, 1,4-hexadiene, methyl (meth)acrylate, ethyl (meth)acrylate, butyl (meth)acrylate, 2-ethylhexyl (meth)acrylate, trifluoroethyl (meth)acrylate, tetrafluoropropyl (meth)acrylate, dibutyl maleate, dibutyl fumarate, diethyl maleate, methoxymethyl (meth)acrylate, ethoxyethyl (meth)acrylate, methoxyethoxyethyl (meth)acrylate, cyanomethyl (meth)acrylate, 2-cyanoethyl (meth)acrylate, 1-cyanopropyl (meth)acrylate, 2-ethyl-6-cyanohexyl (meth)acrylate, 3-cyanopropyl (meth)acrylate, hydroxyethyl (meth)acrylate, hydroxyethyl (meth)acrylate, hydroxypropyl (meth)acrylate, glycidyl (meth)acrylate and dimethylaminoethyl (meth)acrylate.

11. The latex composition for dip-forming of claim 1 comprising the a) carboxylic acid modified-nitrile based copolymer latex and the b) carboxylic acid modified-nitrile based copolymer latex in 80% by weight to 99% by weight with respect to a total weight of the composition, and a solid concentration of 10% to 40% by weight with respect to the total weight of the composition.

12. The latex composition for dip-forming of claim 1, which has a pH of 8 to 12.

13. A dip-formed article prepared from the latex composition for dip-forming of claim 1.

14. The dip-formed article of claim 13, which has nitrogen content of 6.69% by weight to 8.94% by weight based on a total weight of the dip-formed article.

15. The dip-formed article of claim 13, which is one or more types of molded articles selected from the group consisting of an examination glove, a condom, a catheter, an industrial glove, a household glove and a health care product.

* * * * *